United States Patent

Fleck et al.

[11] 4,252,604
[45] Feb. 24, 1981

[54] BIS-(TRIAZINYLAMINO)-STILBENESULPHONIC ACIDS

[75] Inventors: Fritz Fleck, Bottmingen; Hans R. Schmid, Riehen, both of Switzerland

[73] Assignee: Sandoz Ltd., Basel, Switzerland

[21] Appl. No.: 829,241

[22] Filed: Aug. 30, 1977

Related U.S. Application Data

[63] Continuation of Ser. No. 411,484, Oct. 31, 1973, abandoned, which is a continuation of Ser. No. 175,761, Aug. 27, 1971, abandoned.

[30] Foreign Application Priority Data

Sep. 16, 1970 [CH] Switzerland .............. 13721/70
Dec. 3, 1970 [CH] Switzerland .............. 17875/70

[51] Int. Cl.³ .............. C07D 403/12; C09B 23/00; D21H 3/80
[52] U.S. Cl. .............. 162/162; 252/301.23; 542/436; 542/461; 427/158
[58] Field of Search .............. 260/240 B; 542/432, 542/436, 461; 162/162

[56] References Cited

U.S. PATENT DOCUMENTS

| | | | |
|---|---|---|---|
| 3,018,287 | 1/1962 | Fleck | 542/461 |
| 3,600,385 | 8/1971 | Loffelman et al. | 542/461 |
| 3,954,740 | 5/1976 | Fringeli | 542/461 |

FOREIGN PATENT DOCUMENTS 1008457 10/1965 United Kingdom .............. 542/461

OTHER PUBLICATIONS

Derwent Belgian Patents Report No. 6/69, Gp. 2, p. 2 (1969).

*Primary Examiner*—John D. Randolph
*Attorney, Agent, or Firm*—Gerald D. Sharkin; Richard E. Vila; Thomas C. Doyle

[57] ABSTRACT

Bis-(triazinylamino)-stilbenesulphonic acids

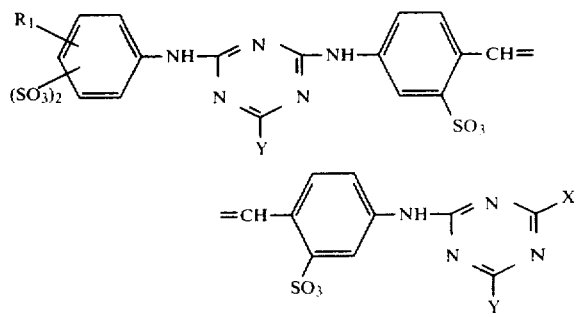

wherein
X is optionally substituted $NH_2$

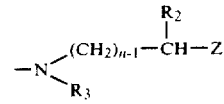

Y is a radical of formula
Z is $-COOR_4$, $-CO-C_mH_{2m+1}$, $-CN$ or

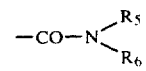

$R_1$ is H, halogen, alkyl or alkoxy,
$R_2$ is H or alkyl,
$R_3$ is H, optionally substituted alkyl, cycloalkyl or phenyl or

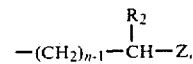

$R_4$ is optionally substituted alkyl,
$R_5$ and $R_6$ are H, alkyl, hydroxyalkyl or form together with N a heterocycle
m is a whole number from 1 to 5 and
n is 1 or 2,
are optical brighteners suitable for cellulosic fibres, polyamide and polyurethane fibres and paper.

14 Claims, No Drawings

BIS-(TRIAZINYLAMINO)-STILBENESULPHONIC ACIDS

This is a continuation of application Ser. No. 411,484, filed Oct. 31, 1973, which in turn is a continuation of application Ser. No. 175,761, filed Aug. 27, 1971 both now abandoned.

This invention relates to new bis-(triazinylamino)-stilbenesulphonic acids of formula

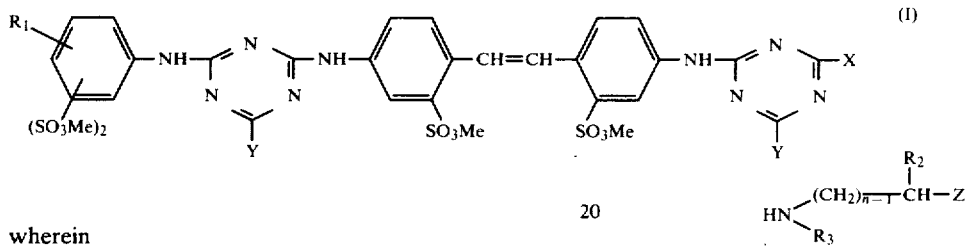

wherein
X stands for an amino group which may be substituted,
Y for a radical of formula

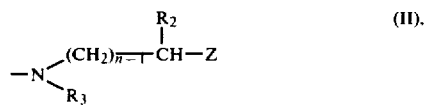

Z for $-COOR_4$, $-CO-C_mH_{2m+1}$, or in particular $-CN$ or

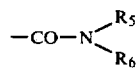

$R_1$ for hydrogen, a lower alkyl or alkoxy radical or a halogen atom,
$R_2$ for hydrogen or a lower alkyl radical,
$R_3$ for hydrogen, a lower alkyl, hydroxyalkyl, hydroxyalkoxyalkyl or alkoxyalkyl radical or a cycloalkyl radical which may be substituted by alkyl or an alkylaminoalkyl radical which may be substituted by hydroxyl or alkoxy groups, an aralkyl or aryloxyalkyl radical, a phenyl radical which may be substituted by lower alkyl or alkoxy groups or by halogen, or a radical of formula

$R_4$ for a lower alkyl radical which may be substituted by hydroxyl, alkoxy, phenyl or phenoxy.
$R_5$ and $R_6$, independently of each other, each stands for a hydrogen atom or a lower alkyl or hydroxyalkyl radical, or $R_5$ and $R_6$ together with the nitrogen atom for a heterocyclic radical,
Me for hydrogen, an alkali metal or an alkaline-earth metal, an ammonium group which may be substituted or aluminium,
m for a whole number from 1 to 5, and
n for 1 or 2.

The process for the production of the new bis-(triazinylamino)-stilbenesulphonic acids comprises reacting 2 mols of a cyanuric halide in any desired order with (a) 1 mol of 4,4'-diaminostilbene-2,2'-disulphonic acid or of a salt of this acid, (b) 1 mol of an aminobenzenedisulphonic acid which may be substituted or of a salt of this acid, (c) 1 mol of ammonia or of a primary or secondary amine, and (d) 2 mols of an amine of formula (IV)

$$HN\begin{matrix}R_2\\|\\(CH_2)_{\overline{n-1}}CH-Z\\R_3\end{matrix}$$

or of a mixture of amines of formula (IV); or reacting 1 mol of a cyanuric halide in any desired order with (a) 1 mol of 4-amino-4'-nitrostilbene-2,2'-disulphonic acid or of a salt of this acid, (b) 1 mol of an aminobenzenedisulphonic acid which may be substituted or of a salt of this acid, (c) 1 mol of an amine of formula (IV) or of a mixture of these amines, then reducing the nitro group, reacting the amino group with 1 mol of a cyanuric halide, and reacting further the dihalogenotriazinyl compound in any desired order with (d) 1 mol of ammonia or of a primary or secondary amine and (e) 1 mol of an amine of formula (IV) or of a mixture of amines of formula (IV).

Examples of suitable aminobenzenedisulphonic acids, substituted if desired, are 1-amino-2-methylbenzene-4,5- and -4,6-disulphonic acid, 1-amino-3-methylbenzene-2,4- and -4,6-disulphonic acid, 1-amino-4-methylbenzene-3,5-disulphonic acid, 1-amino-3-chlorobenzene-4,6-disulphonic acid, 1-amino-4-chlorobenzene-3,6-disulphonic acid, 1-amino-2-methyl-3-chlorobenzene-4,6-disulphonic acid, 1-aminobenzene-3,5-disulphonic acid and 1-aminobenzene-2,4- and -2,5-disulphonic acid, of which the three last named acids are preferred.

The lower alkyl and alkoxy groups may contain 1 to 5 carbon atoms. Fluorine, bromine and in particular chlorine atoms may be named as suitable halogen atoms.

The radical X represents preferably the amino group or the radical of a primary or secondary aliphatic amine which has 1 to about 8 carbon atoms and may bear substituents such as hydroxyl, alkoxy or hydroxyalkoxy groups. Examples of such amines are methyl-, ethyl-, iso-propyl-, n-propyl, n-butyl, n-hexyl-, 2-hydroxyethyl-, 2-hydroxypropyl-amine, N,N'-bis-(β-hydroxyethyl)-propylenediamine, 3-methoxypropyl-, 2-(β-hydroxyethoxy)-ethyl-, N-methyl-N-hydroxyethyl-, di-(hydroxyethyl)-and di-(2-hydroxypropyl-1)-amine, the radical of aromatic amines, preferably of the benzene series, which may bear 1 or 2 lower alkyl or alkoxy groups, halogen atoms, cyano groups, aminocarbonyl or alkoxycarbonyl groups, carboxyl groups or sulphonic acid groups, such as aminobenzene, 1-amino-3-and -4-chlorobenzene, 1-amino-2- and -4-methoxy- and -ethoxy-benzene, 1-amino-2-, -3- and -4-methylbenzene, 1-amino-2-, -3- and -4-cyanobenzene, 1-amino-2-, -3- and -4-aminocarbonylbenzene, -methoxycarbonylbenzene and -ethoxycarbonylbenzene, 1-amino-2-, -3- and -4-carboxybenzene, 1-aminobenzene-3- and -4-sulphonic acid, 1-aminobenzene-3,5-, -2,4- and -2,5-disulphonic acid, the radicals of heterocyclic, non-aromatic amines which contain nitrogen and may contain oxygen and are bound through the nitrogen atom to the triazine ring, such as pyrrolidine, piperidine, hexamethyleneimine and morpholine. The radical X may also be a radical of formula (II).

$R_3$ represents hydrogen or a lower alkyl radical such as methyl, ethyl, n-propyl, n-amyl, n-butyl, iso-amyl, a cycloalkyl radical which may bear lower alkyl radicals, such as cyclohexyl and 4-methylcyclohexyl, a hydroxyalkyl, alkoxyalkyl or hydroxyalkoxyalkyl radical such as 2-hydroxyethyl, 2-hydroxypropyl, 3-methoxypropyl, 3-ethoxypropyl, 3-butoxypropyl, 2-(2'-hydroxyethoxy)-ethyl, an alkylaminoalkyl radical which may be substituted by hydroxyl or alkoxy groups such as 2-(2'-hydroxyethylamino)-ethyl, an aralkyl or aryloxyalkyl radical such as benzyl, phenylethyl or phenoxyethyl, a phenyl radical which may be substituted by lower alkyl or alkoxy groups or by halogen atoms such as phenyl, 2-, 3- and 4-methylphenyl, 2- and 4-methoxy- or -ethoxyphenyl, 3- or 4-chlorophenyl, 4-bromo- or 4-fluorophenyl, 2,5-dichlorophenyl, 2,4-or 2,5-dimethylphenyl, 4-ethyl-, 4-tert. amyl- or 4-tert. butylphenyl.

If $R_3$ stands for a radical of formula (III) it is a lower alkyl radical which may bear the substitutents designed Z, for example 2-cyanethyl, 2-cyanopropyl, 2-oxopropyl, 2-oxobutyl, 3-oxobutyl, 2-aminocarbonylethyl, 2-dimethylaminocarbonylethyl, 2-diethylaminocarbonylethyl, 2-morpholinocarbonylethyl, 2-methoxycarbonylethyl, 2-ethoxycarbonylethyl, 2-n-butoxycarbonylethyl, 2-(2-hydroxyethoxycarbonyl)-ethyl, 2-(2'-hydroxypropoxycarbonyl)-ethyl, 2-(2'-ethoxyethoxycarbonyl)-ethyl, 2-(2'-butoxyethoxycarbonyl)-ethyl, 2-benzyloxycarbonylethyl, 2-(2'-phenylethoxycarbonyl)-ethyl and 2-(2'-phenoxyethoxycarbonyl)-ethyl.

The amines of formula (IV) used as intermediates can be produced by reaction of amines of formula $$R_3-NH_2 \quad (V)$$

with acrylonitrile, the unsubstituted or substituted alkyl esters or amides of acrylic acid, or with the corresponding derivatives of methacrylic acid, or with vinylalkyl ketones such as vinyl methyl ketone, at temperatures in the range of 20° C. to 100° C.

The reaction of the cyanuric halides, e.g. cyanuric bromide or chloride, with the amino compounds can be carried out in aqueous medium with the cyanuric halide suspended in water only, or in aqueous-organic medium, the halide being dissolved in an organic solvent such as acetone, benzene, toluene or chlorbenzene, and the aqueous solution of the amino compound then dropped into the solution. The addition of a dispersing agent can accelerate the rate of reaction and lead to products of higher purity.

If the substituent X represents the radical of an aromatic aminosulphonic acid or another water soluble amine, the products are in many cases obtained in greater purity when the first halogen atom is reacted with the amine or mixture of amines and the second halogen atom subsequently condensed with the 4,4'-diaminostilbene-2,2'-disulphonic acid. The first halogen atom of the cyanuric halide is replaced at 0°-15° C. and in the pH region of 3 to 7. Condensation of the second halogen atom is best carried out in the temperature range of 20° to 60° C. at a weakly acid to weakly alkaline reaction, e.g. in the ph range of 4 to 8, while the third halogen atom is reacted at 80°-100° C. and in the pH range of 4 to 10.

The hydrogen halide set free in the reaction is neutralized with an alkali such as an alkali-metal hydroxide, carbonate or bicarbonate, or with a tertiary organic amine such as tri-(2-hydroxyethyl)-amine.

The nitro group can be reduced, for example, by treatment with an aqueous sodium sulphide or sodium hydrogen sulphide solution, preferably at temperatures in the range of 60° C. to 90° C., or by acidification of the solution with hydrochloric, sulphuric or acetic acid and treatment with zinc powder or iron turnings or powder at 50°-100° C., preferably 80°-100° C.

The optical brighteners produced by the process of this invention are isolated by precipitation with salt or acid or by evaporation of the reaction solution, on which they are obtained in powder form. Alternatively, after separation of the salts they can be worked up in form of liquid preparations by the addition of a dissolving assistant such as a glycol, glycol ether, formamide, acetamide, urea, or a mono-, di- or tri-(2-hydroxyethyl)-or -(2-hydroxypropyl)-amine.

Interesting optical brighteners of formula (I) have the formula

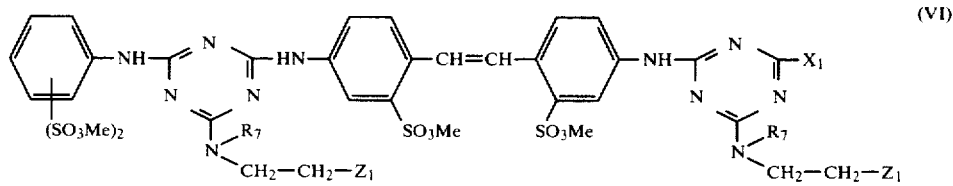

(VI)

wherein $X_1$ stands for $-NH_2$, a phenylamino group which may be substituted by methyl, methoxy, chlorine, cyano or $-SO_3Me$, or a radical

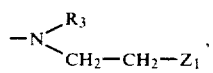

$Z_1$ for $-CN$ or

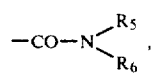

$R_7$ for hydrogen, a lower alkyl, hydroxyalkyl or alkoxyalkyl radical, an alkylaminoalkyl radical which may be substituted by hydroxyl or alkoxy groups, or a radical $-CH_2-CH_2-Z_1$, and Me, $R_5$ and $R_6$ have the meaning given above.

Especially interesting brighteners are of formula

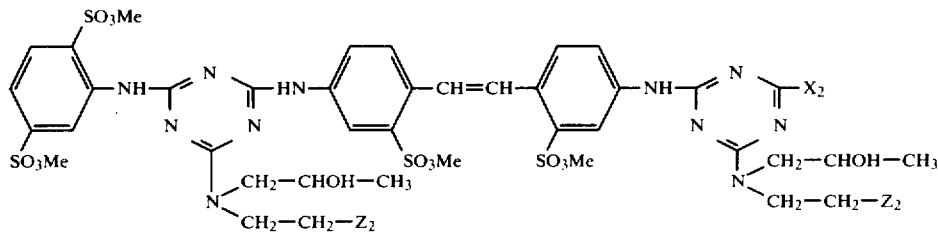

wherein $Z_2$ stands for —CN or —CO—$NH_2$ and $X_2$ for —$NH_2$, phenylamino, 2,5-disulphophenylamino or

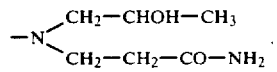

The optical brighteners produced in conformity with this invention are suitable for brightening natural and regenerated cellulosic fibres such as cotton, linen, hemp, ramie, jute, viscose rayon, viscose staple fibre and cuprammonium rayon, natural and synthetic polyamide and polyurethane fibres such as wool, silk, hair, polyamide 6, polyamide 9, polyamide 11, polyamide 12, polyamide 66, polyamide 610, polyamide 6.66, the polyamide from decane-1,10-dicarboxylic acid and 4,4'-diaminodicyclohexylmethane, and the polyurethane fibres described in Textilveredlung 3 11, pp. 663,673 (1968), and paper, particularly by coating methods. Owing to their high solubility and relatively low substantivity they can be applied to paper by the dipping technique and to textile fabrics by the padding technique without reduction in the strength of the application medium. Their good stability to acids and aluminium ions is an important asset for the brightening of paper in the stock before formation. They are compatible with the binders and fillers used for the manufacture of coated papers and produce good effects on these paper grades. Further, they are fully stable in the strongly acid liquors containing synthetic resins which are used for crease resistant finishes on cotton, and to the magnesium and zinc salts used as catalysts in finishes of this type.

The salts of the optical brighteners of this invention can be extended with the commonly used hydrophilic compounds such as polyvinyl alcohol, polyethylene glycols, acylated polyethylene glycols, polyvinyl pyrrollidones or urea, which in many cases appreciably increases the brightening effect. The disclosed brighteners can be applied in combination with known brighteners to produce special effects.

In relation to the nearest comparable compounds described in the British Pat. No. 1008457 and the published Netherlands patent application No. 6 917 378 (referred to in Derwent Netherlands Patents Report Vol. R No. 25 Textiles, Paper, Cellulose, Page 1 (1970) the compounds of this invention show better substantivity and better wash fastness, which is reflected in higher effectiveness and greater stability to acids. Also they are very suitable for pad application, whereas the compounds disclosed in the published Japanese patent application No. 11,072/65 (referred to in Derwent Japanese Patents Report Vol. 4 No. 23 (1965) Textiles and Dyeing page 1). are not suitable for padding.

The principal uses of the new compounds thus comprise the optical brightening of textiles of natural and regenerated cellulosic fibres, either by padding or by application from exhaust baths or synthetic resin finishing liquors, of synthetic polyamide fibres by application from acid baths or in the spinning melt, and of paper by application in the stock or by coating methods after sheet formation.

Further details of the compounds of this invention are contained in the following Examples, which illustrate the invention without limiting its scope. The parts and percentages given therein are by weight and the temperatures in degrees centigrade. The parts by volume in relation to the parts be weight are as milliliters to grammes.

EXAMPLE 1

A solution of 190 parts of cyanuric chloride in 800 parts by volume of acetone is run in 10 minutes with good stirring into 5000 parts of ice-water. In the course of 1 hour a solution of 253 parts of 1-aminobenzene-2,5-disulphonic acid and 106 parts of calcined sodium carbonate in 1500 parts of water is dropped into the suspension at 0°–5° with stirring. The pH is held at 3 to 4 by dropping in 15% sodium carbonate solution. During the addition the suspension goes slowly into solution. Stirring is continued at 0°–5° until the diazo reaction indicates that no further primary aromatic amino groups are present. A solution of 185 parts of 4,4'-diaminostilbene-2,2'-disulphonic acid and 53 parts of calcined sodium carbonate in 1500 parts of water is added, the pH adjusted to 7 with 15% sodium carbonate solution and the solution held at 30° until the diazo reaction is negative. 205 Parts of β-(β'-hydroxypropylamino)-propionic acid amide are added to the clear solution, then its pH is increased to 9–10 with 15% sodium carbonate solution, and the temperature slowly increased to 95°–100° with distillation of the acetone. The solution is held at this temperature for about 90 minutes with reflux, the pH being maintained at 9–10 during this time by the addition of further sodium carbonate solution. Subsequently 3500 parts of sodium chloride are added to the clear solution, which is then allowed to cool. A pale yellow product settles out, which is filtered with suction and vacuum dried. It has the formula

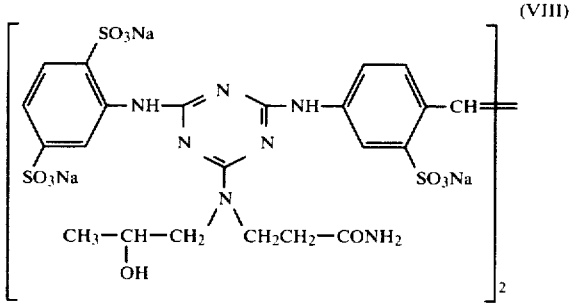

(VIII)

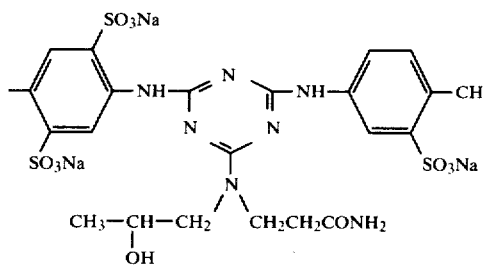

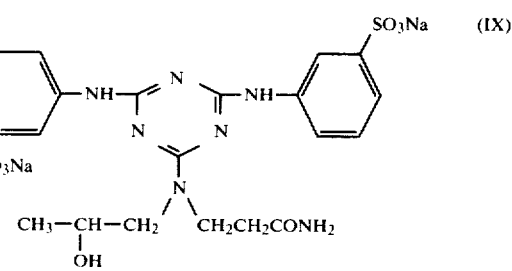

(IX)

The aforenamed propionic acid amide is obtained by stirring 71 parts of acrylic acid amide in 75 parts of mono-isopropanolamine at 40°, with continued stirring for 1 hour at this temperature.

Optical brighteners with comparable properties are obtained when in place of the 205 parts of β-(β'-hydroxypropylamino)-propionic acid amide, 185 parts of β-(β'-hydroxyethylamino)-propionic acid amide, 225 parts of β-(3'-methoxypropylamino) -propionic acid amide, 247 parts of β-[2'-(2"-hydroxyethoxy)-ethylamino]-propionic acid amide, 180 parts of β-(β'-hydroxypropylamino)-propionitrile, 200 parts of β-(3'-methoxypropylamino)-propionitrile or 222 parts of β-]2'-(2"-hydroxyethoxy)-ethylamino]-propionitrile are employed. The aforenamed propionitriles are obtained in the same way as the propionic acid amides, using acrylonitrile in place of acrylic acid amide.

In place of aniline-2,5-disulphonic acid, the isomeric aniline- 2,4-disulphonic acid can be used with equal success.

EXAMPLE 2

A solution of 190 parts of cyanuric chloride in 800 parts by volume of acetone is allowed to flow in 10 minutes with thorough stirring into 5000 parts of ice-water. With continued stirring, a solution of 126 parts of 1-aminobenzene-2,5-disulphonic acid and 53 parts of calcined sodium carbonate in 750 parts of water is dropped into the solution at 0°-5° in the course of 30 minutes. Stirring is continued until no further diazotizable amino groups are indicated. At the same time the pH is maintained at 3-4 with 15% sodium carbonate solution and the temperature of the reaction mixture held at 0°-5°. In the next 30 minutes a solution of 86 parts of 3-aminobenzenesulphonic acid and 27 parts of calcined sodium carbonate in 200 parts of water is dropped into the reaction solution, the pH being maintained constant at 3-4 by the further addition of 15% sodium carbonate solution. On completion of the reaction a solution of 185 parts of 4,4'-diaminostilbene-2,2'-disulphonic acid and 53 parts of calcined sodium carbonate in 1500 parts of water are added. The further procedure is as in Example 1. The product has the formula In place of 3-aminobenzenesulphonic acid, 4-aminobenzenesulphonic acid or aminobenzene can be used with equal good results.

EXAMPLE 3

A solution of 190 parts of cyanuric chloride in 800 parts by volume of acetone is run in 10 minutes with thorough stirring into 2000 parts of ice-water. A solution of 185 parts of 4,4'-diaminostilbene-2,2'-disulphonic acid and 53 parts of calcined sodium carbonate in 1500 parts of water is dropped into the resulting suspension in 1 hour at 0°-5°. When the diazo reaction indicates that no further primary aromatic amino groups are present a solution of 126 parts of 1-aminobenzene-2,5-disulphonic acid and 53 parts of calcined sodium carbonate in 750 parts of water is added in 30 minutes at 20°-30°. At the same time 15% sodium carbonate solution is added to keep the pH at 7. As soon as no further diazotizable amine is indicated, 250 parts of a 25% ammonia solution are added. The mixture is then stirred for 2 hours at 40° and the excess ammonia removed by means of a water-jet vacuum pump. 205 Parts of β-(β'-hydroxypropylamino)-propionic acid amide are added, followed by sufficient 15% sodium carbonate solution to increase the pH to 9-10, and the mixture is then held for 3 hours at 95°-100°. The product thus obtained is dried in an atomizer drier. It has the formula

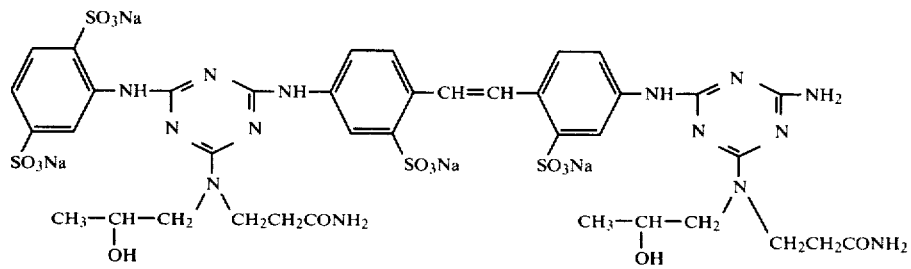

(X)

In place of the ammonia solution, 46 parts of a 35% aqueous solution of monomethylamine, 33 parts of a 70% aqueous solution of monoethylamine, 35 parts of diethylamine, 31 parts of 2-hydroxyethylamine or 53 parts of di-(2-hydroxyethyl)-amine can be used, on which products with similar properties are obtained. The ammonia solution can be replaced by a further 73 parts of β-(β'-hydroxypropylamino)-propionic acid amide with equally good results.

In place of the β-(β'-hydroxypropylamino)-propionic acid amide, the secondary amines bearing negative substituents named in Example 1 can be employed to give products of comparable quality.

EXAMPLE 4

A solution of 190 parts of cyanuric chloride in 800 parts by volume of acetone is run in 10 minutes into 5000 parts of ice-water with thorough stirring. In 1 hour a solution of 267 parts of 1-amino-2-methylbenzene-4,6-disulphonic acid and 106 parts of calcined sodium carbonate in 1500 parts of water is dropped into the suspension at 10°–15° with stirring. The pH is maintained at 3–4 by adding 15% sodium carbonate solution dropwise at the same time. The suspension goes slowly into solution during the addition. Stirring is continued at 10°–15° until the diazo reaction shows that no further primary aromatic amino groups are present. Then a solution of 185 parts of 4,4'-diaminostilbene-2,2'-disulphonic acid and 53 parts of calcined sodium carbonate in 1500 parts of water is added, the pH adjusted to 7 with 15% sodium carbonate solution, and the solution maintained at 30° until the diazo reaction is negative. 205 Parts of β-(β'-hydroxypropylamino)-propionic acid amide are added to the clear solution, the pH is increased to 9–10 with 15% sodium carbonate solution, and the solution raised slowly to 95°–100° with distillation of the acetone. The solution is boiled for about 90 minutes with reflux, the pH being held at 9 10 by adding further sodium carbonate solution. Finally, 3500 parts of sodium chloride are added to the clear solution and it is allowed to cool. The pale yellow product settles out and is filtered with suction and vacuum dried. It has the formula

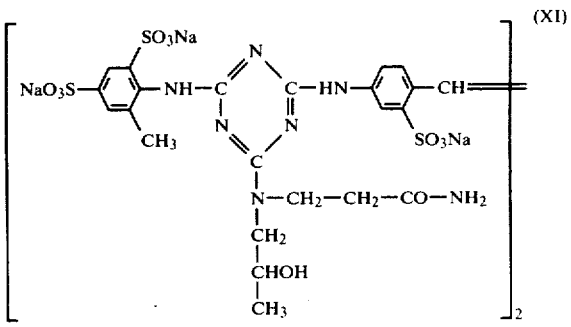

In place of β-(β'-hydroxypropylamino)-propionic acid amide, one of the β-aminopropionic acid amides or β-aminopropionitriles named at the end of Example 1 can be used, which give optical brighteners of equally good quality.

In the following table further optical brighteners of formula

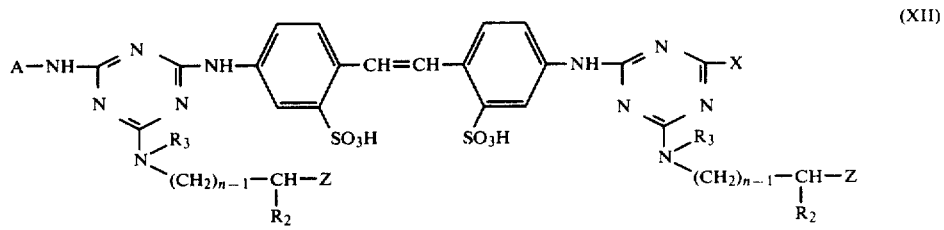

conforming to this invention are specified by the meanings of the symbols A, $R_2$, $R_3$, X, Z and n.

TABLE

| Example No. | A | $R_2$ | $R_3$ | Z | X | n |
|---|---|---|---|---|---|---|
| 5 | 2,4-Disulphophenyl | $CH_3$ | $-C_2H_4-OH$ | $-CO-NH_2$ | 2,4-Disulphophenyl-amino | 2 |
| 6 | '' | H | '' | $-CN$ | '' | 2 |
| 7 | '' | H | '' | $-CO-NH_2$ | 3 Sulphophenylamino | 2 |
| 8 | '' | H | H | '' | Di-(2-hydroxyethyl)-amino | 2 |
| 9 | 3,5-Disulphophenyl | H | $-CH_3$ | '' | 3,5 Disulphophenylamino | 2 |
| 10 | 3-Chloro-4,6-disulphophenyl | H | $-CH_2-CHOH-CH_3$ | '' | 3 Chloro-4,6-disulphophenylamino | 2 |
| 11 | 2,5-Disulphophenyl | H | $-C_2H_5$ | '' | 4 Sulphophenylamino | 2 |
| 12 | '' | H | $-C_2H_4-OH$ | '' | '' | 1 |
| 13 | '' | H | $-C_2H_4-OH$ | $-CN$ | '' | 1 |
| 14 | 2,4-Disulphophenyl | $CH_3$ | $-CH_2-CHOH-CH_3$ | $-CN$ | 2,4-Disulphophenylamino | 2 |
| 15 | 2,5-Disulphophenyl | $CH_3$ | '' | $-CN$ | 2,5-Disulphophenylamino | 2 |
| 16 | '' | $CH_3$ | '' | $-CO-NH_2$ | '' | 2 |
| 17 | '' | H | $-C_2H_5$ | '' | '' | 1 |
| 18 | '' | H | $-CH_3$ | '' | 4-Sulphophenylamino | 1 |
| 19 | '' | H | $-CH_3$ | '' | Phenylamino | 1 |
| 20 | '' | H | H | $-COOCH_3$ | 3-Sulphophenylamino | 1 |
| 21 | '' | H | H | $-COO-C_4H_{9n}$ | '' | 1 |
| 22 | '' | H | H | $-CO-NH-CH_3$ | 2,5-Disulphophenylamino | 1 |
| 23 | '' | H | H | $-CO-NH-C_4H_{9n}$ | '' | 1 |
| 24 | '' | H | H | $-CO-N(CH_3)_2$ | '' | 1 |
| 25 | '' | H | H | $-CO-N(C_2H_5)_2$ | '' | 1 |
| 26 | '' | H | $-nC_4H_9$ | '' | '' | 2 |
| 27 | '' | H | $-C_2H_4-OH$ | $-CONH-C_2H_4OH$ | '' | 2 |
| 28 | '' | H | '' | '' | '' | 1 |
| 29 | 3,5-Disulphophenyl | H | $-C_2H_4-OH$. | $-CN$ | 3,5-Disulphophenylamino | 1 |

TABLE -continued

| Example No. | A | $R_2$ | $R_3$ | Z | X | n |
|---|---|---|---|---|---|---|
| 30 | " | H | $CH_3$ | $-CO-NH_2$ | " | 1 |
| 31 | 2,4-Disulphophenyl | H | " | " | 2,4-Disulphophenylamino | 1 |
| 32 | " | H | $-nC_4H_9$ | " | " | 1 |
| 33 | 2,5-Disulphophenyl | H | 3-Methoxypropyl | " | 2,5-Disulphophenylamino | 1 |
| 34 | " | H | " | " | " | 2 |
| 35 | " | H | $-CH_2-CHOH-CH_3$ | " | 4-Methylphenylamino | 2 |
| 36 | " | H | " | " | " | 1 |
| 37 | " | H | " | " | 3-Chlorophenylamino | 1 |
| 38 | " | H | " | " | " | 2 |
| 39 | " | H | " | " | 4-Methoxyphenylamino | 2 |
| 40 | " | H | " | " | " | 1 |
| 41 | " | $CH_3$ | $C_2H_5$ | " | 2,5-Disulphophenylamino | 2 |
| 42 | " | H | $-C_2H_4OH$ | " | N-$\beta$-Hydroxyethyl-N-$\beta$-aminocarbonylethyl-amino | 2 |
| 43 | " | H | $CH_3$ | " | N-Methyl-N-$\beta$-aminocarbonylethyl-amino | 2 |
| 44 | 2,4-Disulphophenyl | H | 2-Methoxyethyl | " | 4-Sulphophenylamino | 2 |
| 45 | 2,5-Disulphophenyl | H | " | " | " | 2 |
| 46 | " | H | 2-Ethoxyethyl | " | 2,5-Disulphophenylamino | 2 |
| 47 | " | H | 2-n-Butoxyethyl | " | " | 2 |
| 48 | " | H | 2-Cyanethyl | $-CN$ | " | 2 |
| 49 | " | H | 2-Aminocarbonylethyl | $-CO-NH_2$ | " | 2 |
| 50 | " | H | 2-Morpholinocarbonylethyl | $-CO-N\begin{smallmatrix}C_2H_4\\C_2H_4\end{smallmatrix}O$ | " | 2 |
| 51 | " | H | 2-Dimethylaminocarbonylethyl | $-CO-N(CH_3)_2$ | " | 2 |
| 52 | " | H | Methylaminocarbonylethyl | $-CO-NH-CH_3$ | " | 2 |
| 53 | " | H | $-C_2H_4-CN$ | $-CO-N(C_2H_4OH)_2$ | Phenylamino | 2 |
| 54 | " | H | 2-Cyanopropyl | $-CO-NH_2$ | 3-Sulphophenylamino | 2 |
| 55 | " | H | 2-Methoxycarbonylethyl | $-CO-O-CH_3$ | " | 2 |
| 56 | " | H | 4-n-Butoxycarbonylethyl | $-COOC_4H_9$ | 2,5-Disulphophenylamino | 2 |
| 57 | " | H | n-Amyl | $-CO-NH_2$ | 2,5-Disulphophenylamino | 2 |
| 58 | " | H | Cyclohexyl | " | " | 2 |
| 59 | " | H | Benzyl | " | " | 2 |
| 60 | " | H | $-C_2H_4OH$ | $-CO-CH_3$ | " | 2 |
| 61 | " | H | " | $-CO-NH_2$ | $-NH-CH_3$ | 2 |
| 62 | " | H | $-CH_2-CHOH-CH_3$ | $-CO-NH-C_4H_{9n}$ | $-NH-C_2H_4OH$ | 2 |
| 63 | " | H | " | $-CO-N(C_4H_{9n})_2$ | 2,5-Disulphenylamino | 2 |
| 64 | " | H | $-C_2H_4-OH$ | " | " | 1 |
| 65 | " | H | $-C_2H_4OH$ | $-CO-NH_2$ | Di-(2-hydroxypropyl)-amino | 2 |
| 66 | " | H | Phenyl | $-CO-NH_2$ | 2,5-Disulphophenylamino | 2 |
| 67 | " | H | $CH_3$ | " | " | 2 |
| 68 | " | H | " | $-CO-N\begin{smallmatrix}C_2H_4\\C_2H_4\end{smallmatrix}CH_2$ | " | 1 |
| 69 | " | H | $-CH_2-CHOH-CH_3$ | $-CO-N\begin{smallmatrix}C_2H_4\\C_2H_4\end{smallmatrix}O$ | " | 2 |
| 70 | " | H | 3-Dimethylaminopropyl | " | " | 2 |
| 71 | " | H | $-CH_3$ | $-CO-NH_2$ | $-NH_2$ | 1 |
| 72 | " | H | 4-Methylphenyl | " | " | 2 |
| 73 | " | H | $-CH_2-CHOH-CH_3$ | $-CO-N(CH_2-CHOH-CH_3)_2$ | $-NH-CH_2-CHOH-CH_3$ | 2 |
| 74 | " | H | " | $-CO-NH_2$ | $-N(nC_4H_9)_2$ | 2 |
| 75 | " | H | " | " | $-NH-(CH_2)_3-O-CH_3$ | 2 |
| 76 | " | H | " | " | $-N\begin{smallmatrix}CH_3\\C_2H_4-OH\end{smallmatrix}$ | 2 |
| 77 | " | H | " | " | 4-Carboxyphenylamino | 2 |
| 78 | " | H | " | " | 4-Cyanophenylamino | 2 |
| 79 | " | H | " | " | 4-Methoxycarbonxylphenylamino | 2 |
| 80 | " | H | " | " | 4-Aminocarbonylphenylamino | 2 |
| 81 | " | H | 2-(2'-Hydroxyethylamino)-ethyl | " | 2,5-Disulphophenylamino | 2 |
| 82 | " | H | 2-(2'-Hydroxyethoxy)-ethyl | " | 4-Sulphophenylamino | 2 |

TABLE -continued

| Example No. | A | R$_2$ | R$_3$ | Z | X | n |
|---|---|---|---|---|---|---|
| 83 | " | H | 2-Benzyloxycarbonylethyl | —CO—O—CH$_2$— | 2,5-Disulphophenylamino | 2 |
| 84 | " | H | —CH$_2$CHOH—CH$_3$ | —CONH$_2$ | —NH—C$_6$H$_{13n}$ | 2 |

APPLICATION EXAMPLE A

A cotton fabric is conveyed through a bath of 240 parts of dimethylolethylene urea, 28 parts of 48.5% sulphuric acid, 2 parts of the brightener of Example 1 and 730 parts of water, expressed between a pair of rollers to retain 100% of its weight of liquor, and dried at 90° to 8% residual moisture content. The fabric is rolled up and stored for 17 hours at room temperature. Afterwards it is rinsed with cold water, neutralized wiht a 2 g/l solution of anhydrous sodium carbonate, rinsed again with cold water, expressed and dried at 100°. The treated fabric shows a brilliant white effect of neutral shade.

APPLICATION EXAMPLE B

A cotton fabric is conveyed through a solution of 8 parts of the brightener of Example 2 in 1000 parts of water, expressed to an increase of 100% on the dry weight, and dried at 60°-70°. A good white effect is obtained. If 8 parts of a polyethylene glycol with a molecular weight of 5000–6000 is added to the solution, the brightening effect is greatly intensified.

APPLICATION EXAMPLE C

A sized paper made from sulphite pulp is coated with a paste of the composition:
66 parts china clay
33 parts water
10 parts of 50% dispersion of a butadiene-styrene copolymer
5 parts of a 10% casein solution
0.3 part of a 10% solution of the brightener of Example 1.

The degree of whiteness shown by the coated paper is appreciably greater than the whiteness of a coating without optical brightener. The whiteness can be enhanced further by including in the coating composition 1% of a 10% solution of a polyethylene glycol of molecular weight 5000–6000.

APPLICATION EXAMPLE D

A solution of 0.3 part of one of the brighteners of Example 3 in 300 parts of water is added to a suspension of 100 parts of bleached sulphate pulp beaten to 40 degrees Schopper-Riegler in 4000 parts of water containing 10 parts of aluminium sulphate. The suspension is carefully stirred for 30 minutes, sized with a solution of 20 parts of 10% rosin size and 3 parts of aluminium sulphate in 10 parts of water, then diluted with water to 20,000 parts, and converted into sheet. The sheet thus produced is well brightened. This result shows that the brighteners of this invention can be applied in paper stocks at low pH values, which is very important in paper manufacture where backwaters with a high content of aluminium sulphate have to be used.

APPLICATION EXAMPLE E

A coating mixture consisting of 66 parts of china clay, 33 parts of water, 10 parts of a 50% dispersion of a butadiene-styrene copolymer, 1 part of a 10% solution of a polyethylene glycol of molecular weight 5000–6000 and 0.3 part of a 10% solution of a brightener of Example 1 or 2 is mechanically applied to sized paper made from stock consisting of 50% bleached sulphite pulp and 50% mechanical woodpulp. An attractive brightened paper is obtained.

A further addition of 5 parts of a 10% solution of a reduced starch can be included in the above coating mixture, which gives a slight improvement in the brightening effect.

Formulae of representative optical brighteners of the foregoing Examples are as follows:

EXAMPLES 1 penultimate paragraph

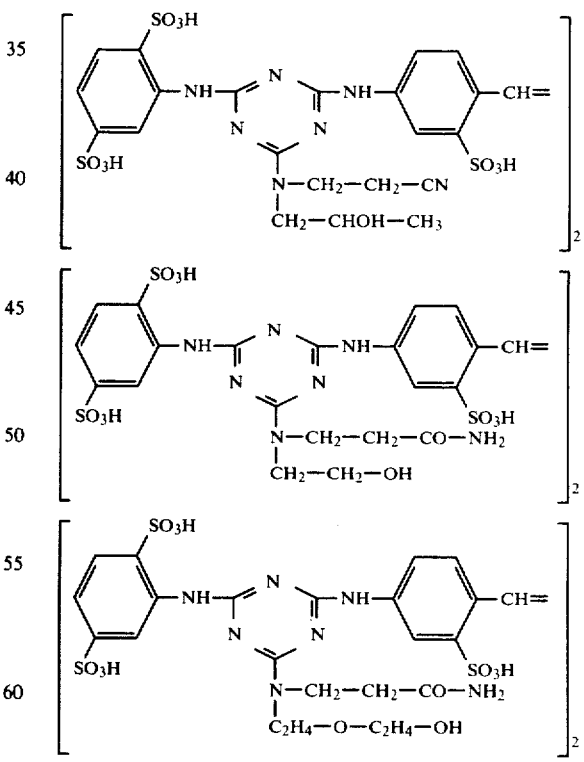

EXAMPLE 2 last paragraph

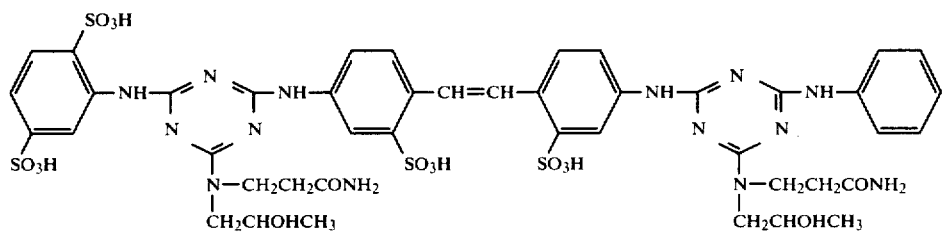

EXAMPLE 3 penultimate paragraph

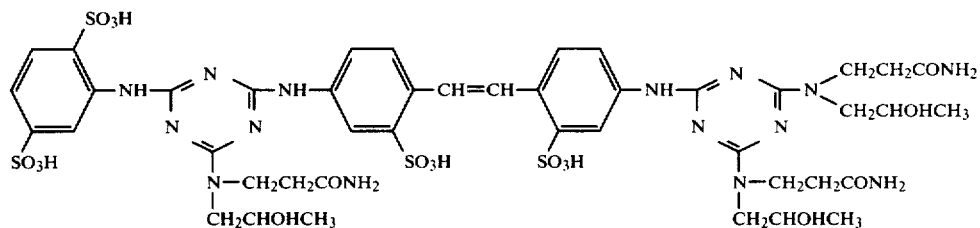

Having thus disclosed the invention what we claim is:
1. A compound of the formula

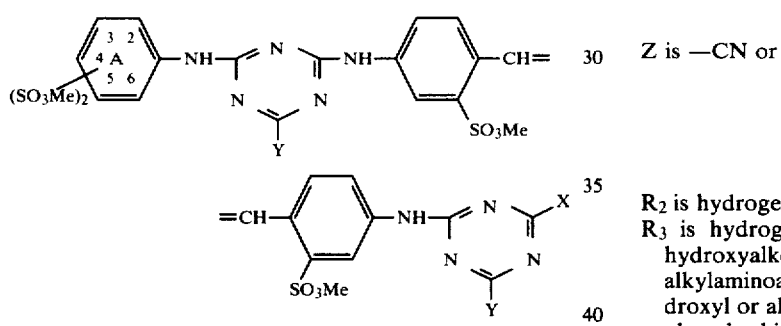

wherein
X is (a) amino; (b) primary and secondary alkyl amino of 1 to 8 carbon atoms, the alkyl portions of which may be substituted by hydroxyl, alkoxy, hydroxyalkoxy, or β-hydroxyethylamino; (c) phenylamino in which the phenyl radical may be mono- or disubstituted by lower alkyl, lower alkoxy, halo, cyano, aminocarbonyl, alkoxycarbonyl, carboxyl, or sulphonic acid; (d) pyrrolidino, (e) piperidino; (f) hexamethyleneimino; (g) morpholino; or (h) a radical Y,
Y is a radical of the formula

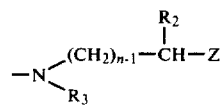

Z is —CN or

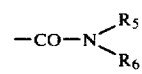

$R_2$ is hydrogen or alkyl,
$R_3$ is hydrogen; alkyl; hydroxyalkyl; alkoxyalkyl; hydroxyalkoxyalkyl; cyclohexyl; alkylcyclohexyl; alkylaminoalkyl which may be substituted by hydroxyl or alkoxy groups; phenalkyl; phenoxyalkyl; phenyl which may be substituted by alkyl, alkoxy or by halogen; or a radical of formula

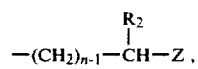

$R_5$ and $R_6$, independently of each other, are hydrogen, alkyl, or hydroxyalkyl, or $R_5$ and $R_6$ together with the nitrogen atom form a piperidino or morpholino radical,
Me is hydrogen, an alkali metal or an alkaline-earth metal, an ammonium group or aluminum,
n is 1 or 2,
any alkyl or alkoxy group contains 1 to 5 carbon atoms unless otherwise specified and the $SO_3Me$ groups on the ring A are in the 3,5-, 2,4- or 2,5-positions.
2. A compound according to claim 1 of the formula (VI)

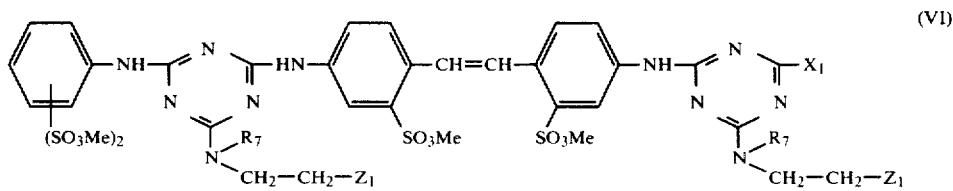

wherein

X₁ stands for —NH₂, a phenylamino group which may be substituted by methyl, methoxy, chlorine, cyano or —SO₃Me, or a radical

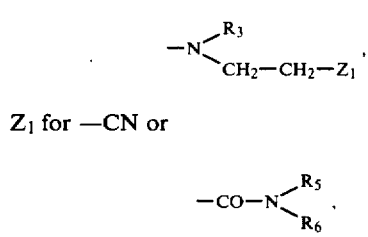

Z₁ for —CN or

—CO—N⟨R₅/R₆, and

R₇ for hydrogen, a lower alkyl, hydroxyalkyl or alkoxyalkyl radical, an alkylaminoalkyl radical which may be substituted by hydroxyl or alkoxy groups, or a radical - —CH₂—CH₂—Z₁.

3. A compound according to claim 2 of the formula

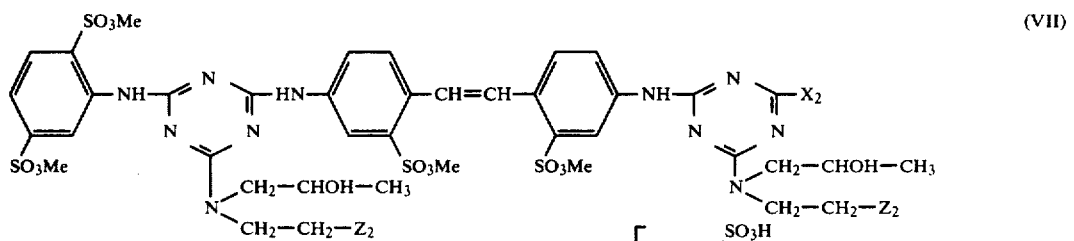

wherein

Z₂ stands for —CN or —CO—NH₂
and
X₂ for —NH₂, phenylamino, 2,5-disulphophenylamino or

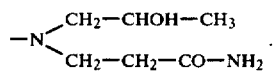

4. The bis-(triazinylamino)-stilbenesulphonic acid according to claim 3 of the formula

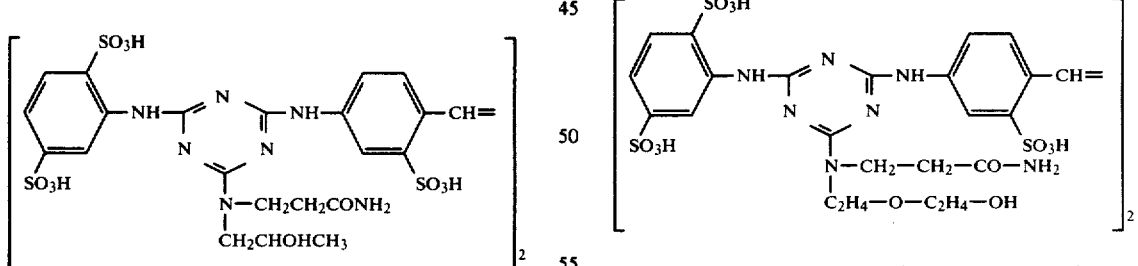

5. The bis-(triazinylamino)-stilbenesulphonic acid according to claim 3 of the formula

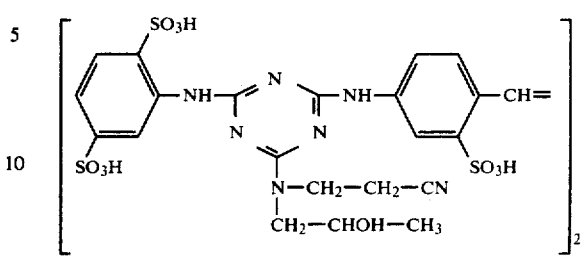

6. The bis-(triazinylamino)-stilbenesulphonic acid according to claim 2 of the formula (VII)

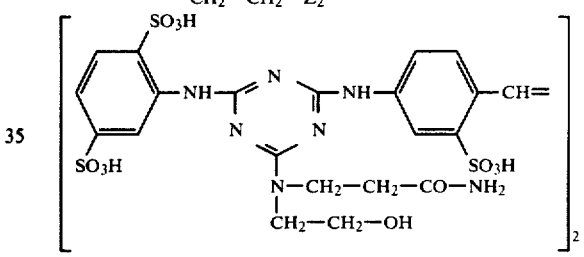

7. The bis-(triazinylamino)-stilbenesulphonic acid according to claim 1 of the formula

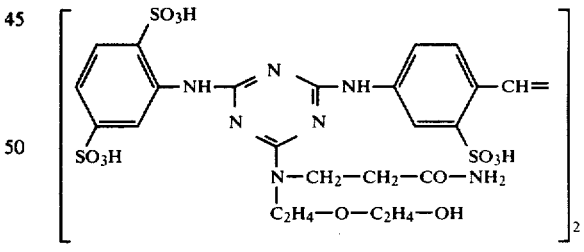

8. The bis-(triazinylamino)-stilbenesulphonic acid according to claim 3 of the formula

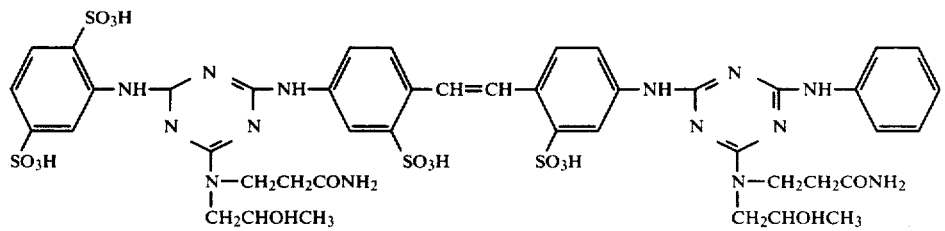

9. The bis-(triazinylamino)-stilbenesulphonic acid according to claim 3 of the formula

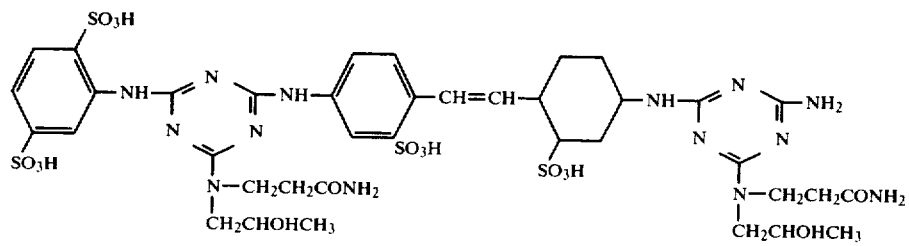

10. The bis-(triazinylamino)-stilbenesulphonic acid according to claim 3 of the formula

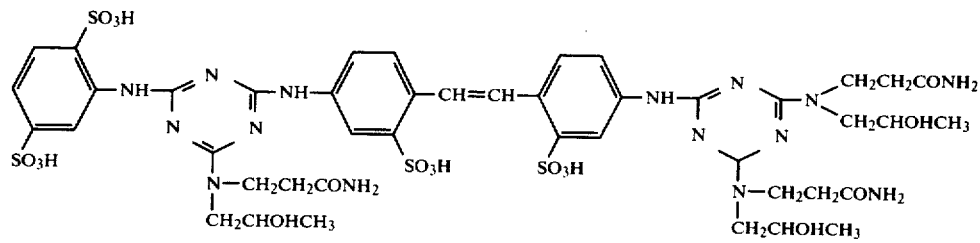

11. A compound according to claim 2 of the formula

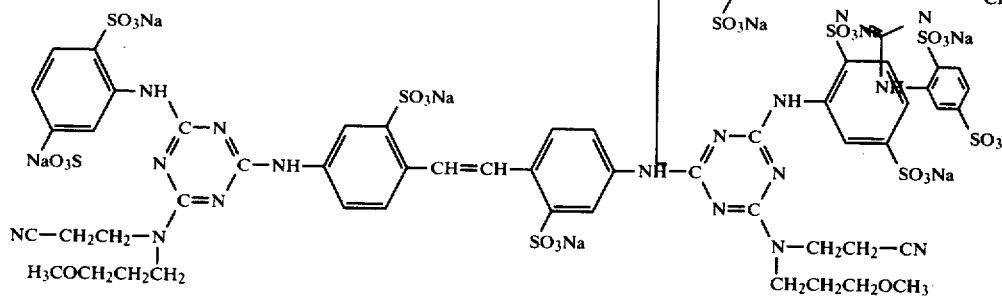

12. A method of treating paper with optical brighteners which comprises incorporating the compound defined in claim 11 into the coating composition for the surface treatment of paper and applying said coating composition to the paper.

13. Paper containing a compound as defined in claim 11.

14. A compound according to claim 1 of the formula